US007477373B2

(12) United States Patent
Miyakawa et al.

(10) Patent No.: US 7,477,373 B2
(45) Date of Patent: Jan. 13, 2009

(54) SURFACE INSPECTION METHOD AND SURFACE INSPECTION DEVICE

(75) Inventors: Kazuhiro Miyakawa, Itabashi-ku (JP); Yoichiro Iwa, Itabashi-ku (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 0 days.

(21) Appl. No.: 11/725,849

(22) Filed: Mar. 20, 2007

(65) Prior Publication Data
US 2007/0229813 A1    Oct. 4, 2007

(30) Foreign Application Priority Data
Mar. 31, 2006   (JP)   ............... 2006-100144

(51) Int. Cl.
*G01N 21/00*   (2006.01)
(52) U.S. Cl. .................................. 356/237.3
(58) Field of Classification Search ........................ None
See application file for complete search history.

(56) References Cited

U.S. PATENT DOCUMENTS

| | | | |
|---|---|---|---|
| 4,468,120 A * | 8/1984 | Tanimoto et al. ......... 356/239.8 |
| 4,922,308 A * | 5/1990 | Noguchi et al. .......... 356/237.4 |
| 6,104,481 A * | 8/2000 | Sekine et al. ............ 356/237.5 |
| 6,411,377 B1 * | 6/2002 | Noguchi et al. .......... 356/237.4 |
| 6,654,111 B2 * | 11/2003 | Isozaki et al. ............ 356/237.3 |
| 6,774,991 B1 * | 8/2004 | Danko ....................... 356/237.4 |
| 6,797,975 B2 * | 9/2004 | Nishiyama et al. ...... 250/559.04 |
| 7,333,192 B2 * | 2/2008 | Nakano et al. ........... 356/237.2 |
| 2005/0133692 A1 | 6/2005 | Watanabe et al. ........... 250/214 |

FOREIGN PATENT DOCUMENTS

| | | |
|---|---|---|
| JP | 2004-271519 | 9/2004 |
| JP | 2005-526239 | 9/2005 |
| WO | 03/073476 | 9/2003 |

OTHER PUBLICATIONS

New Optical Microscope (vol. 1); Laser Microscope; Theory and Practice; Supervised by Tetsuya Fujita, edited by Satoshi Kawata; Gakusai Kikaku Co., Ltd.; Mar. 28, 1995 with partial English translation.

* cited by examiner

Primary Examiner—Michael A Lyons
Assistant Examiner—Gordon J Stock, Jr.
(74) Attorney, Agent, or Firm—Nields & Lemack

(57) ABSTRACT

A surface inspection method for projecting a laser beam to an inspection surface and for scanning and detecting foreign objects or the like on the inspection surface, comprising a step of being had a required number of detecting regions by a photodetector against a projecting site of the laser beam, a step of receiving a detection light at the photodetector so that a detection light intensity is varied between the detecting regions, a step of acquiring a required number of output signals with different detection light intensities on an inspection site, and a step of selecting an output signal which is an unsaturated output signal and has the highest value among the required number of output signals as a surface detection signal.

8 Claims, 7 Drawing Sheets

FEEDING DIRECTION OF THE BEAM ←

CH₁     CHₙ

16

EXAMPLE OF DETECTION LIGHT INTENSITY
AND OUTPUT SIGNAL LEVEL

SURFACE INSPECTION METHOD AND SURFACE INSPECTION DEVICE

BACKGROUND OF THE INVENTION

The present invention relates to a surface inspection method and a surface inspection device for detecting micro-size flaws or foreign objects attached on a surface of a substrate such as a semiconductor wafer or the like.

In the past, in case that micro-size foreign objects attached on a surface or micro-size flaws on a surface are to be detected, detection of the foreign objects or the flaws have been carried out by projecting a laser beam to a surface to be inspected and by receiving and detecting a scattering light from the foreign objects or the flaws.

FIG. 8 shows general features of a surface inspection device. As an object to be inspected, a silicon wafer 1 is shown.

The silicon wafer 1 is held at horizontal position by a substrate chuck 2, and the substrate chuck 2 is rotated at a predetermined rotation speed by a motor 3.

An inspection light projecting system 5 and a scattering light receiving system 6 are positioned against an inspection surface 4 of the silicon wafer 1. The inspection light projecting system 5 projects an inspection light from a light source unit to the inspection surface 4. For instance, a laser beam 7 is projected at an incident angle as required, and a reflected light 7' of the laser beam 7 reflected by the inspection surface 4 is detected by a reflection light detector 8. Light intensity of the reflected light 7' of the laser beam 7 detected at the reflection light detector 8 is sent by feedback in order to keep the projection intensity of the laser beam 7 at a constant level.

The scattering light receiving system 6 has an optical axis, which crosses an optical axis of the inspection light projecting system 5. On the optical axis, a lateral scattering light detector 9 and a forward scattering light detector 11 are arranged. The lateral scattering light detector 9 and the forward scattering light detector 11 have different crossing directions and different crossing angles. The lateral scattering light detector 9 and the forward scattering light detector 11 detect the scattering light occurred by a foreign object or a flaw when the laser beam 7 is projected and issue electric signals to match the received light amount.

For the inspection of the inspection surface 4, the inspection surface is rotated by the motor 3 under condition that the laser beam 7 is projected on the inspection surface 4. Further, the inspection surface 4 is shifted in radial direction of the silicon wafer 1 at a predetermined pitch (a predetermined speed). The projecting point of the laser beam 7 is shifted in radial direction while rotating, and the laser beam 7 scans over the entire surface of the inspection surface 4. When the laser beam 7 passes through the foreign objects or the flaws, the reflected light is scattered, and the lateral scattering light detector 9 and the forward scattering light detector 11 receive a scattering light 12 respectively.

The scattering light 12 thus received is converted to an electric signal by a photoelectric conversion element. Further, the electric signal is amplified by an amplifier and is processed as a foreign object signal and is stored in a storage unit as a detection result.

The examples of output signals of the lateral scattering light detector 9 and the forward scattering light detector 11 are shown in FIG. 9. Normally, the output signal contains a signal component S and a direct current component D. In case that the inspection surface 4 has a smooth surface as it is polished well or the like, and there is little scattering reflection on the inspection surface 4 itself, the direct current component D is low. In case that the inspection surface 4 has rough surface and there is much scattering reflection on the inspection surface 4, the direct current component D is appeared highly.

Next, FIG. 10 is a diagram to show a relation between the detection light intensity and the signal output level when the lateral scattering light detector 9 and the forward scattering light detector 11 receive the light. Normally, the inspection light intensity and the signal output level are in a proportional relation as shown by a curve A in FIG. 10. When the inspection light intensity exceeds a predetermined value and the signal output level reaches a proportional limit (a measurement limit), the output signal comes to lose linear and is turned to saturated state. Therefore, a range I where the proportional relation is maintained, is a measurement range (a dynamic range) of the detector.

However, when the inspection surface 4 has rough surface (e.g. rear surface of the wafer), or when the inspection surface 4 is a wafer surface with a metal film formed on the wafer surface, irregular reflection on the surface itself is increased. As a result, the direct current component D as shown in FIG. 9 increases and the detection light intensity may exceed the measurement range. Then it is substantially impossible to perform the measurement.

To solve this problem, as a method to extend the measurement range, there is a method to logarithmically amplify the signal by using a logarithmic amplifier. In case that the signal is amplified by using the logarithmic amplifier, the signal output level is shown as a curve B in FIG. 10.

In case that the logarithmic amplification is performed, the more the detection light intensity increases, the less the increasing ratio of the signal level is. As the comparison between the curve A and the curve B shows, when the detection light intensity reaches at the measurement limit, the value of the detection light intensity increases by IA. That is, the measurement range is extended by IA.

However, when logarithmic amplification is performed, the output signal with the detection light intensity of low level is emphasized. For example, in case that the light intensity is P, the signal output level is higher in the curve B by ΔS compared with the curve A. Accordingly, the noise of low level is detected higher, and the S/N ratio tends to be decreased. In case that the detection signal range is in high frequency band, higher S/N ratio and higher responsiveness are required on the logarithmic amplifier. Therefore, the logarithmic amplifier becomes expensive.

A surface inspection device is described in JP-A-2004-217519. The device to extend the dynamic range by logarithmic amplification is described in: JP-A-2005-526239, and "New Optical Microscope (Vol. 1); Laser Microscope; Theory and Practice"; Supervised by Tetsuya FUJITA, edited by Satoshi KAWATA; Gakusai Kikaku Co., Ltd.; Mar. 28, 1995; p. 116.

SUMMARY OF THE INVENTION

It is an object of the present invention to provide a surface inspection method and a surface inspection device, which are simple in arrangement and have wide dynamic range and by which it is possible to perform surface inspection with high S/N ratio even in case that there are much scattering light from the inspection surface.

The present invention provides a surface inspection method for projecting a laser beam to an inspection surface and for scanning and detecting foreign objects or the like on the inspection surface, comprising a step of being had a required number of detecting regions by a photodetector against a projecting site of the laser beam, a step of receiving a detection light at the photodetector so that a detection light intensity is varied between the detecting regions, a step of acquiring a required number of output signals with different detection light intensities on an inspection site, and a step of selecting an output signal which is an unsaturated output signal and has the highest value among the required number of output signals as a surface detection signal. Also, the present invention provides the surface inspection method as described above, wherein the laser beam is projected to have such light intensity distribution that the light intensity varies at the projected site, and a required number of detecting regions are set so that detection light intensities are varied. Further, the present invention provides the surface inspection method as described above, wherein the light amount is adjusted by an optical filter so that the detection light intensity is varied between the detecting regions. Also, the present invention provides the surface inspection method as described above, wherein the detecting regions are divided with a predetermined pitch in a direction crossing the scanning direction, and a feeding pitch to perpendicularly cross the scanning direction is equal to the dividing pitch.

Further, the present invention provides a surface inspection device, comprising an inspection light projecting system for projecting a laser beam to an inspection surface, a scattering light receiving system for detecting scattering lights, and an arithmetic operation unit for performing calculation to detect foreign objects or the like based on scattering light detection output of the scattering light receiving system, wherein the scattering light receiving system has a required number of detecting regions and detects detection lights so that the scattering light intensities to receive the detection light are varied between the detecting regions, and the arithmetic operation unit selects an unsaturated scattering light detecting output with the highest value among a plurality of scattering light detecting output obtained at the same site as a surface inspection signal, and foreign objects or the like are inspected according to the surface inspection signal. Also, the present invention provides the surface inspection device as described above, wherein the inspection light projecting system projects the laser beam to have such light intensity distribution that the light intensity varies at the projected site, and the detecting regions are set so that the detection light intensity is varied. Further, the present invention provides the surface inspection device as described above, wherein an optical filter is provided in the scattering light receiving system so that detection light intensity is varied between the detecting regions. Also, the present invention provides the surface inspection device as described above, further comprising a rotating position detector, a feeding position detector, a photodetector for issuing photodetection signals individually for each region, and a memory unit arranged to match each region, wherein the photodetection signals are stored in each memory unit by associating with the rotating position and the feeding position, the arithmetic operation unit extracts a photodetection signal with the same rotating position and the same feeding position in the each memory unit and selects an unsaturated photodetection signal with the highest value as a surface inspection signal.

According to the present invention, a surface inspection method for projecting a laser beam to an inspection surface and for scanning and detecting foreign objects or the like on the inspection surface, comprises a step of being had a required number of detecting regions by a photodetector against a projecting site of the laser beam, a step of receiving a detection light at the photodetector so that detection light intensity is varied between the detecting regions, a step of acquiring a required number of output signals with different detection light intensities on an inspection site, and a step of selecting an output signal which is an unsaturated output signal and has the highest value among the required number of output signals as a surface detection signal. As a result, dynamic range can be extended for the detection of scattering light and it is possible to detect the scattering light with higher S/N ratio without changing the conventional arrangement of the device and by simple arrangement.

Further, according to the present invention, a surface inspection device, comprises an inspection light projecting system for projecting a laser beam to an inspection surface, a scattering light receiving system for detecting a scattering light, and an arithmetic operation unit for performing calculation to detect foreign objects or the like based on scattering light detection output of the scattering light receiving system, wherein the scattering light receiving system has a required number of detecting regions and detects detection lights so that the scattering light intensities to receive the detection light are varied between the detecting regions, and the arithmetic operation unit selects an unsaturated scattering light detecting output with the highest value among a plurality of scattering light detecting output obtained at the same site as a surface inspection signal, and foreign objects or the like are inspected based on the surface inspection signal. Thus, dynamic range can be extended for the detection of scattering light and it is possible to detect the scattering light with higher S/N ratio without changing the conventional arrangement of the device and by simple arrangement.

DETAILED DESCRIPTION OF THE PREFERRED EMBODIMENT

Description will be given below on the best mode for carrying out the invention referring to the attached drawings.

Figure 1:
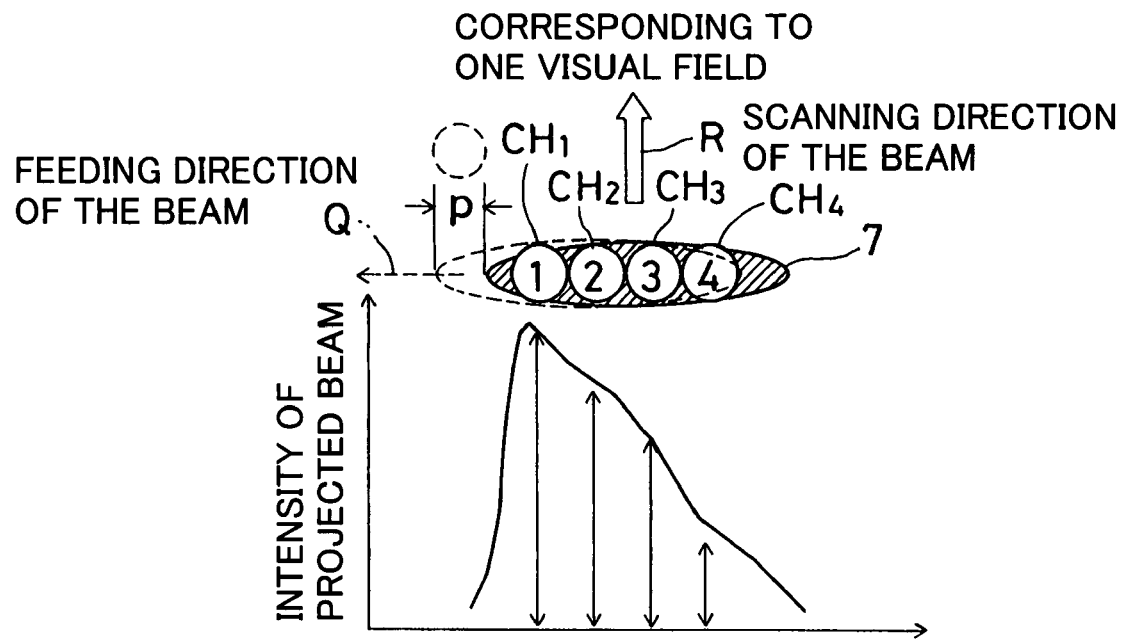
FIG. 1 is a diagram to show a relation between projection range of a laser beam and detecting regions and a relation between projected light intensity distribution and detecting regions in a first embodiment of the present invention.
Figure 2:
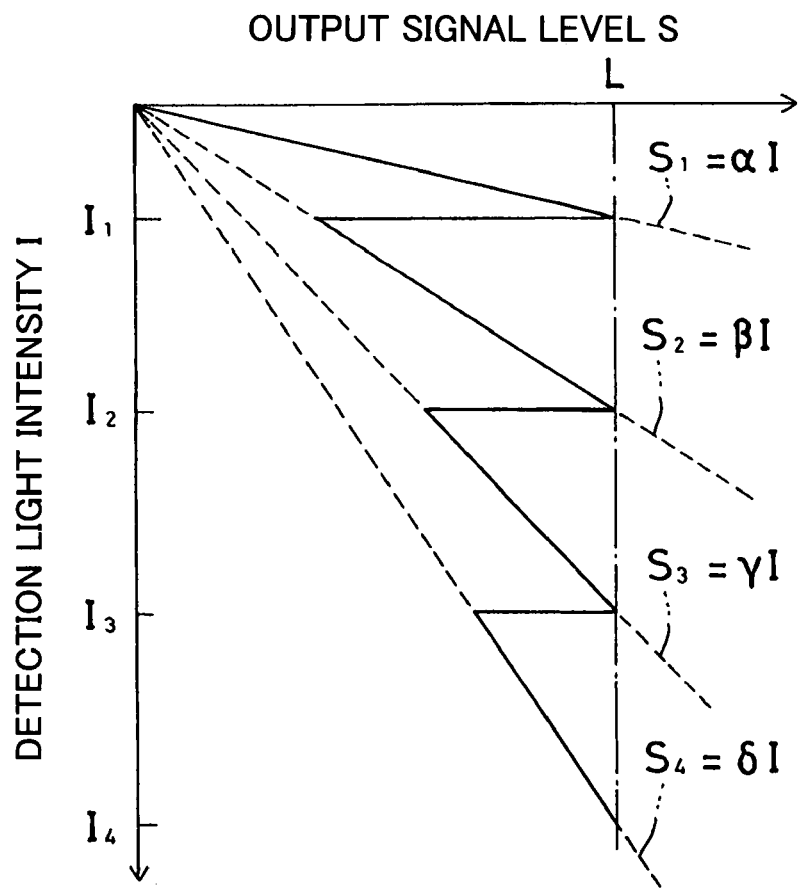
FIG. 2 is a diagram to show a relation between detection light intensity and output signal level in each of the detection regions in the first embodiment of the invention.

Referring to FIG. 1 and FIG. 2, description will be given on a first embodiment of a surface inspection method according to the present invention.

Figure 8:
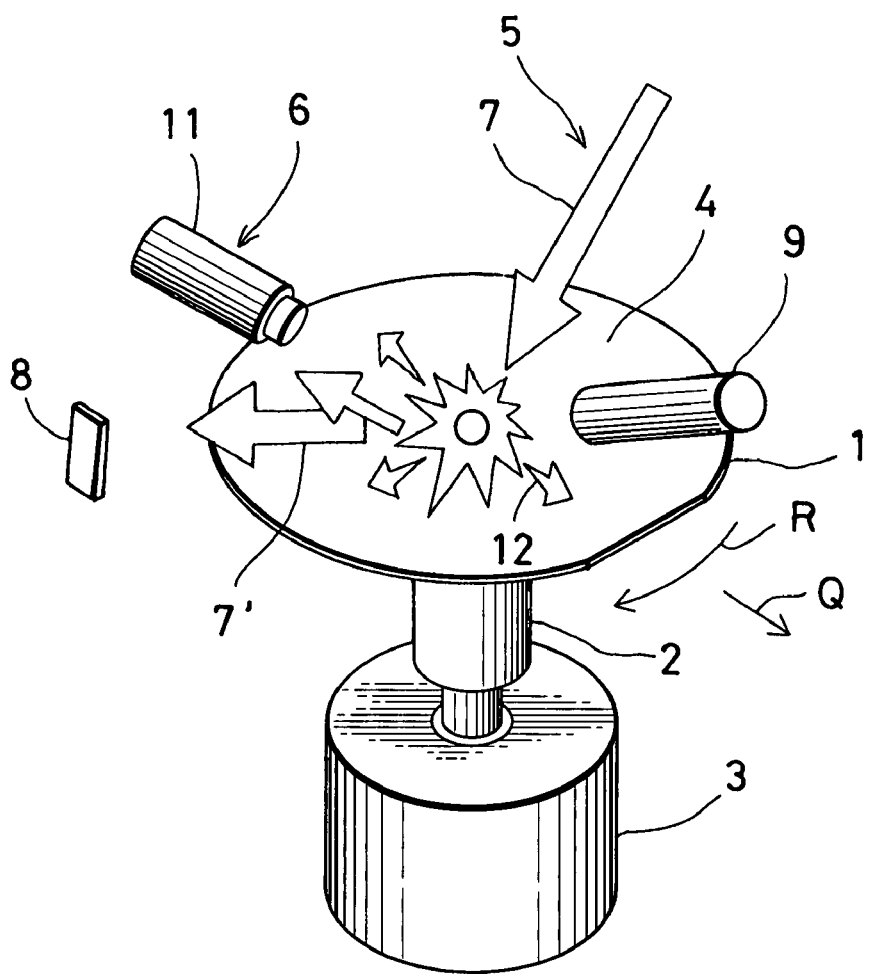
FIG. 8 is a perspective view to show approximate arrangement of the surface inspection device.
Figure 9:
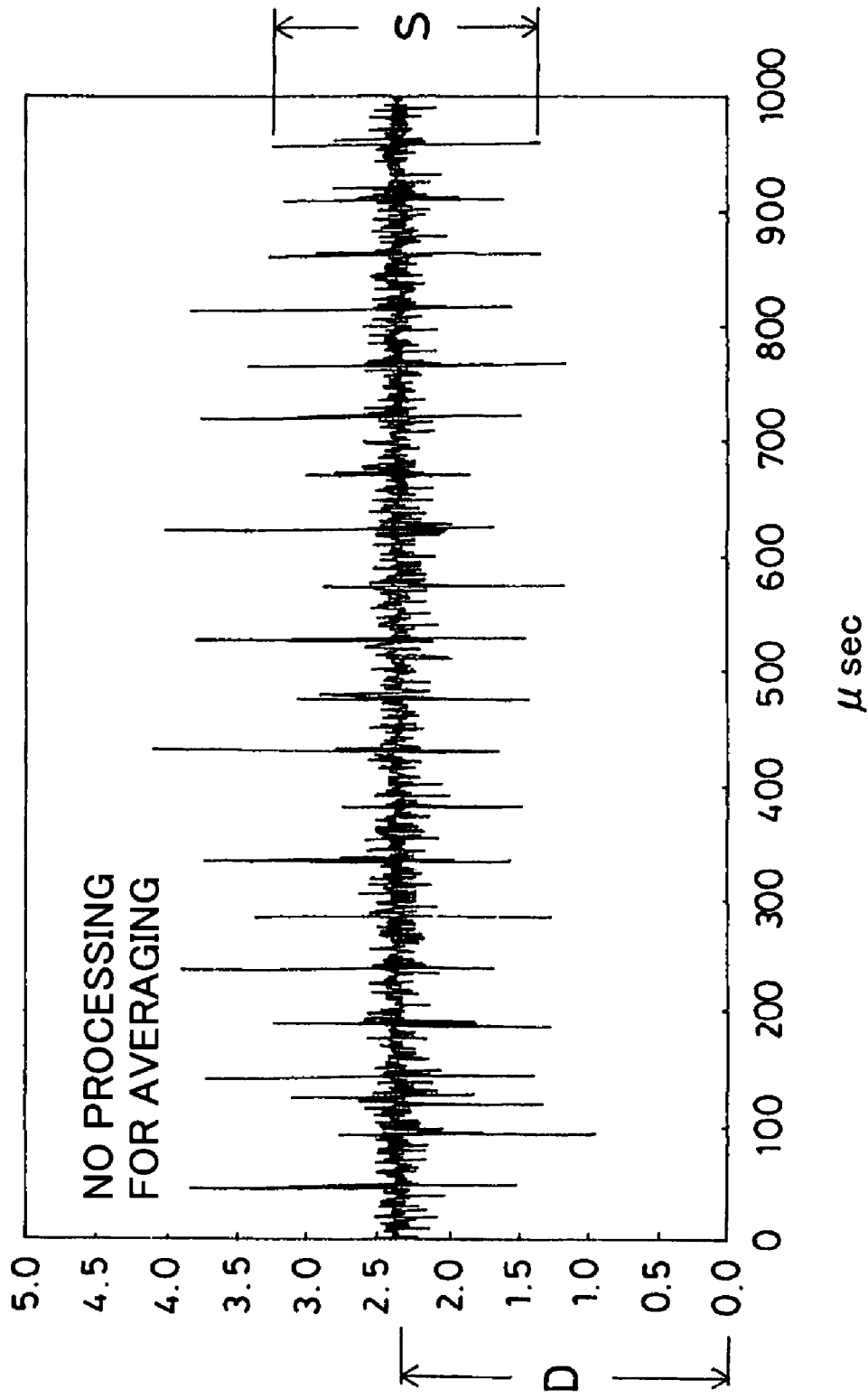
FIG. 9 is a diagram to show an example of an output signal from a conventional type scattering light detector.
Figure 10:
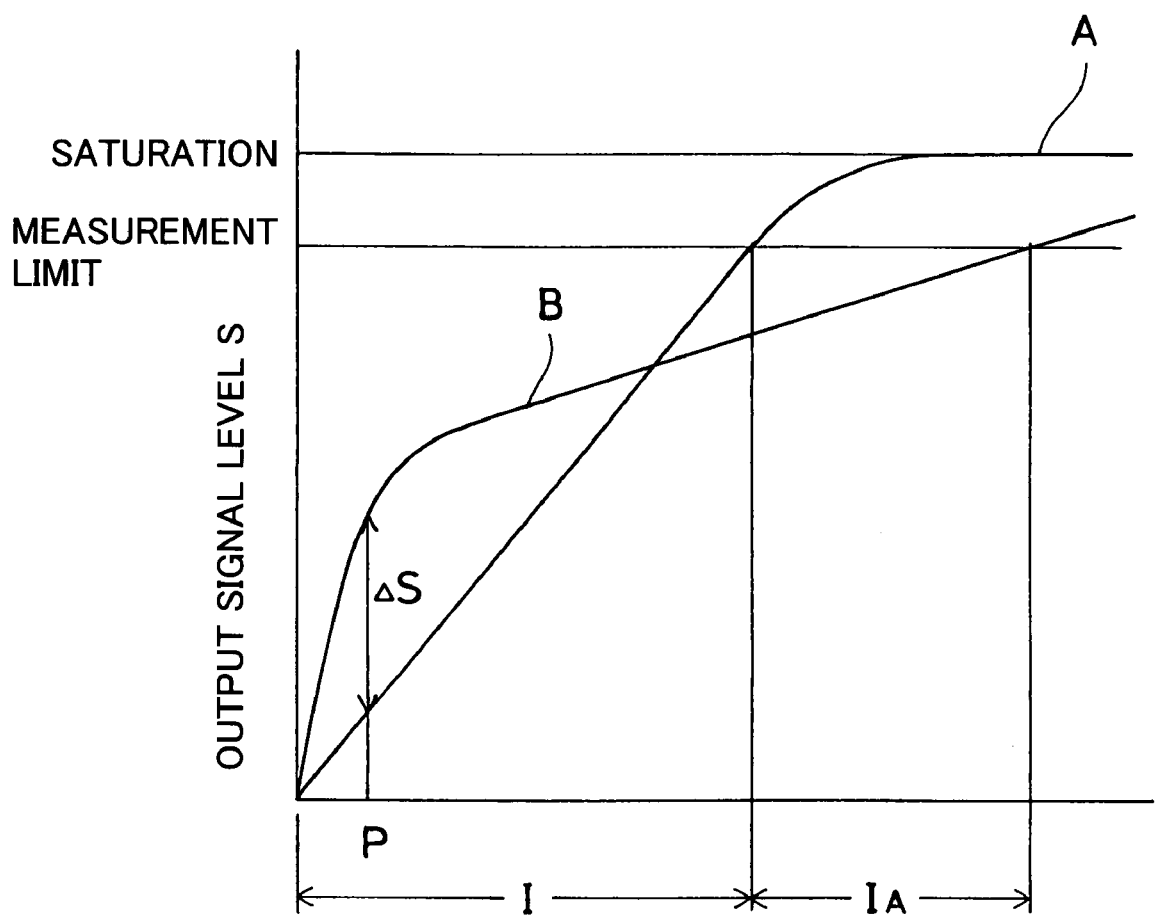
FIG. 10 is a diagram to show a relation between detection light intensity and output signal level in a conventional example.

Basic arrangement of a surface inspection device, in which the surface inspection method according to the present invention is carried out, is the same as arrangement shown in FIG. 8. In FIG. 8, the surface inspections by a lateral scattering light detector 9 and by a forward scattering light detector 11 are carried out in the same manner. Thus, description will be given below on the case where surface inspection is performed by the lateral scattering light detector 9 referring to FIG. 8.

When a laser beam 7 emitted from an inspection light projecting system 5 is projected to an inspection surface 4, a cross-section of luminous fluxes is in oblong elliptical shape as shown in FIG. 1, and the cross-section of luminous fluxes is so designed that the longer axis perpendicularly crosses the scanning direction of the beam, i.e. the longer axis perpendicularly crosses a rotating direction R of a silicon wafer 1. In a photodetecting region of the lateral scattering light detector 9, a required number of detecting regions (in the figure, 4 detecting regions of CH1, CH2, CH3, and CH4) are set up in the direction of the longer axis (feeding direction Q of the beam) so that photodetection can be achieved independently for each detecting region. The detecting regions are positioned to be adjacent to each other, and pitch of the detecting regions is designed to be equal to a distance of shifting of the beam in radial direction when the silicon wafer 1 is rotated by one turn (feeding pitch p).

In the projection light intensity distribution at a point where the laser beam 7 is projected, for instance a peak value is found on a forward portion of the feeding direction of the beam, and the light intensity is gradually decreased toward backward direction.

Detection light intensities S1, S2, S3 and S4 correspond to each of the detecting regions CH1, CH2, CH3 and CH4 respectively. Therefore, under the same reflecting condition when the laser beam 7 is projected, detection light intensities S1, S2, S3 and S4 are in a relation of: S1>S2>S3>S4. Also, if it is supposed that ratio of the detection light intensities is: S1:S2:S3:S4=$\alpha$:$\beta$:$\gamma$:$\delta$, the relation of the detection light intensities S1, S2, S3 and S4 with signal output level is as shown in FIG. 2.

In the figure, the axis I of ordinate represents detection light intensity when it is supposed that detection is performed in the detecting region CH1, and the axis L of abscissa represents a proportional limit (measurement limit) of the detection light intensity I and an output signal level S.

In the surface inspection, the laser beam 7 as shown in FIG. 1 is projected to the inspection surface 4, and the silicon wafer 1 is rotated at a predetermined constant speed. Further, the silicon wafer 1 is shifted in radial direction at a predetermined constant speed. As described above, the moving speed of the silicon wafer is set to such a value that the laser beam 7 is fed in radial direction at a feeding pitch p.

When the laser beam 7 is projected to scan the entire surface of the inspection surface 4, each of the detecting regions CH1, CH2, CH3 and CH4 scans the entire surface of the inspection surface 4 respectively. That is, the inspection surface 4 is scanned 4 times by the detecting regions CH1, CH2, CH3 and CH4.

When the silicon wafer 1 is rotated at a constant speed and the silicon wafer 1 is shifted at a constant speed, shifting time of the feeding pitch p is set to a constant value, i.e. $\Delta t$. After the elapse of the time $\Delta t$, the detecting region at rearward point is replaced by the detecting region at a forward point. For instance, when the condition shown in FIG. 1 is taken as a reference, CH2 is shifted to the position of CH1 after the elapse of the time $\Delta t$. After the elapse of the time 2$\Delta t$, CH3 is shifted to the position of CH1. After the elapse of the time 3$\Delta t$, CH4 is shifted to the position of CH1. Therefore, a photodetection signal at CH1, a photodetection signal at CH2 after the elapse of $\Delta t$, a photodetection signal at CH3 after the elapse of 2$\Delta t$, and a photodetection signal at CH4 after the elapse of 3$\Delta t$ are photodetection signals on the same point on the detection surface 4, and the ratio of the photodetection signals is: S1:S2:S3:S4=$\alpha$:$\beta$:$\gamma$:$\delta$.

Consequently, 4 different output signals are obtained at the same point or site. Output signals of S1, S2, S3 and S4 are outputted respectively. The output signals are positioned on a line respectively, which is represented by S1=$\alpha$I, S2=$\beta$I, S3=$\gamma$I, and S4=$\delta$I. Then, one of the output signals S1, S2, S3 and S4 is selected as a surface inspection signal.

As the selected signal, the output signal is selected of all, which does not exceed a proportional limit (a measurement limit) L and showes the highest value. For instance, when the output signals S1 and S2 exceed the proportional limit and the output signal S3 is within the proportional limit, the output signal S3 is selected as the surface inspection signal.

Therefore, the output signal thus obtained is represented by a curve in serrated form.

If the relation between the size of the flaw and the size of the foreign object, and the values of S1=$\alpha$I, S2=$\beta$I, S3=$\gamma$I, and S4=$\delta$I, is taken in advance as data, the data on the flaw or on the foreign object can be promptly obtained from the selected output signal S and from an output value of the signal.

On the results of total surface scanning at the detecting regions CH1, CH2, CH3 and CH4 on the inspection surface 4, the result of detection of the detecting region CH1, the result of detection of the detecting region CH2 after the elapse of $\Delta t$, the result of detection of the detecting region CH3 after the elapse of 2$\Delta t$, and the result of detection of the detecting region CH4 after the elapse of 3$\Delta t$ are obtained together, and if the data are selected on the inspection sites over the entire surface of the inspection surface 4, surface inspection can be carried out in the range of detection light intensity of 0-I4, and the surface inspection can be performed on an inspection surface with high direct current component such as rough surface, etc.

According to the present invention, measurement range (dynamic range) is extended to the detection light intensity of I1 to I4. The surface inspection device has the same arrangement as the conventional device, and there is no need to use a specific type of amplifier. With the extension of the measurement range, a noise signal of low level is not increased or stressed, and high S/N ratio can be obtained in the range of the detection light intensity of 0 to I4.

Figure 3:
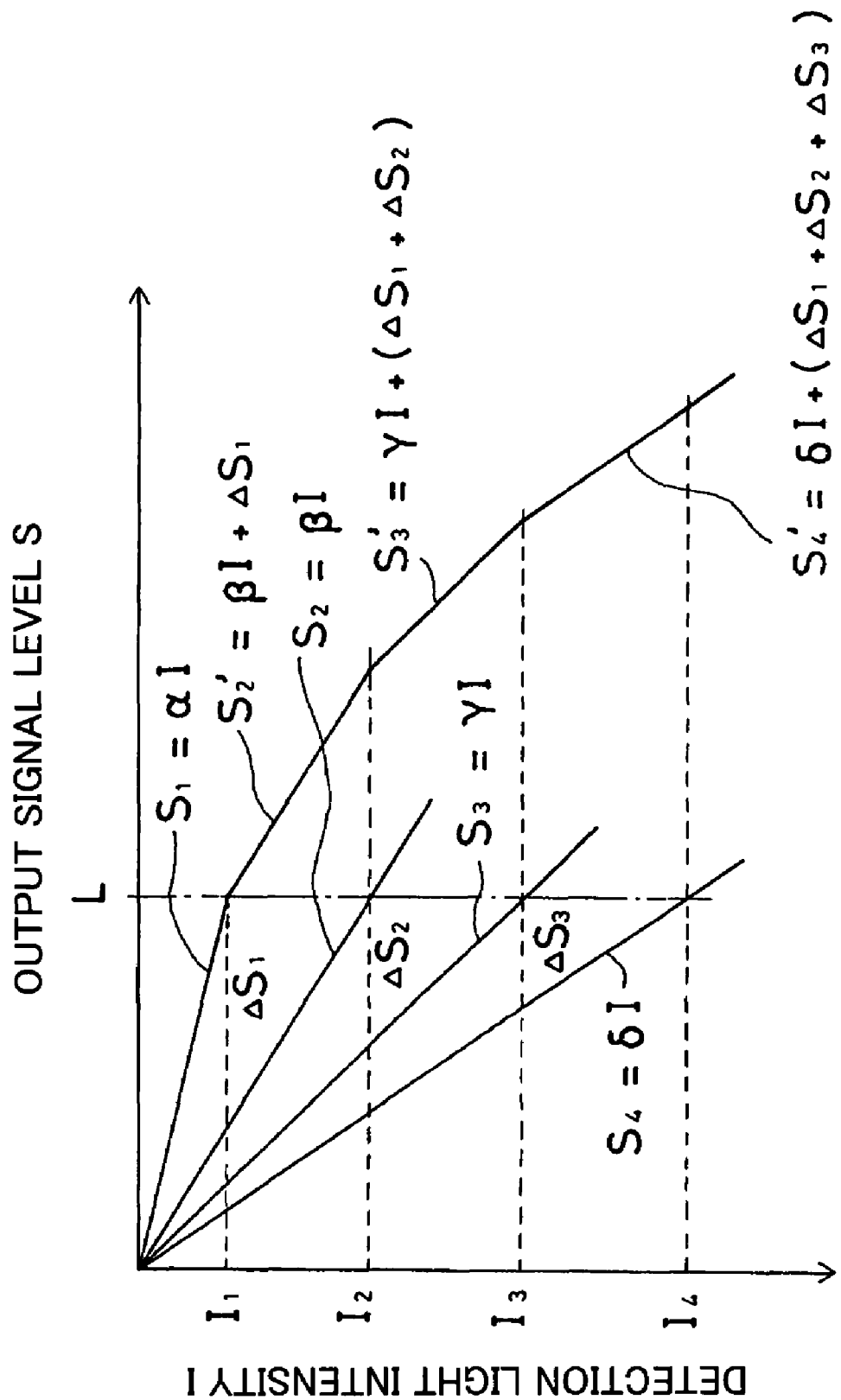
FIG. 3 is a diagram to show a relation between detection light intensity and output signal level in each of the detection regions in a second embodiment of the invention.

Now, referring to FIG. 1 and FIG. 3, description will be given on a second embodiment of the invention.

The following conditions of inspection are the same as in the first embodiment described above. The following conditions of inspection are the relation between the laser beam 7 and the detecting regions CH1, CH2, CH3 and CH4; detection light intensity when the ratio of the detection light intensity is set to: S1:S2:S3:S4=$\alpha$:$\beta$:$\gamma$:$\delta$; detection light intensity when the axis I of ordinate represents detection light intensity when it is supposed that detection is performed in the detecting region CH1; the axis L of abscissa is the proportional limit (the measurement limit) of the detection light intensity I and the output signal level S; inspecting conditions, etc.

In the second embodiment, it is so arranged that the signal output level is increased to match the increase of the detection light intensity.

When the output signal S1 of the detection light received at the detecting region CH1 exceeds the proportional limit (the measurement limit), an output signal S2 of the detection light received at the detecting region CH2 is selected. When the output signal S2 of the detection light received at the detecting region CH2 exceeds the proportional limit (the measurement limit) L, the output signal S3 of the detection light received at the detecting region CH3 is selected. When the output signal S3 of the detection light received at the detecting region CH3 exceeds the proportional limit (the measurement limit) L, the output signal S4 of the detection light received at the detecting region CH4 is selected.

In order that the signal output level is increased to match the increase of the detection light intensity, a deviation $\Delta S1$ is added to the output signal S2. The deviation $\Delta S1$ is a deviation between S1 and S2 when S1 reaches the proportional limit (the measurement limit) L. Thus, the output signal S2 is turned to an output signal S2'.

When the output signal S3 is selected, a deviation $\Delta S2$ is added further. The deviation $\Delta S2$ is a deviation between S2 and S3 when S2 reaches the proportional limit (the measurement limit) L. Thus, the output signal S3 is turned to an output signal S3'.

Similarly, when the output signal S4 is selected, a deviation $\Delta S3$ is added further. The deviation $\Delta S3$ is a deviation between S3 and S4 when S3 reaches the proportional limit (the measurement limit) L. Thus, the output signal S4 is turned to an output signal S4'.

In the second embodiment, the signal output level is increased to match the increase of the detection light intensity. Accordingly, depending on the level of signal output level, the size of the flaw and the size of the foreign object can be identified.

In the second embodiment, too, the measurement range (dynamic range) is extended to the detection light intensities I1 to I4 in appearance. The surface inspection device has the same arrangement as the conventional type device, and there is no need to use a specific type of amplifier. Also, no increase or stress occurs on the noise signal of low level.

Figure 4:
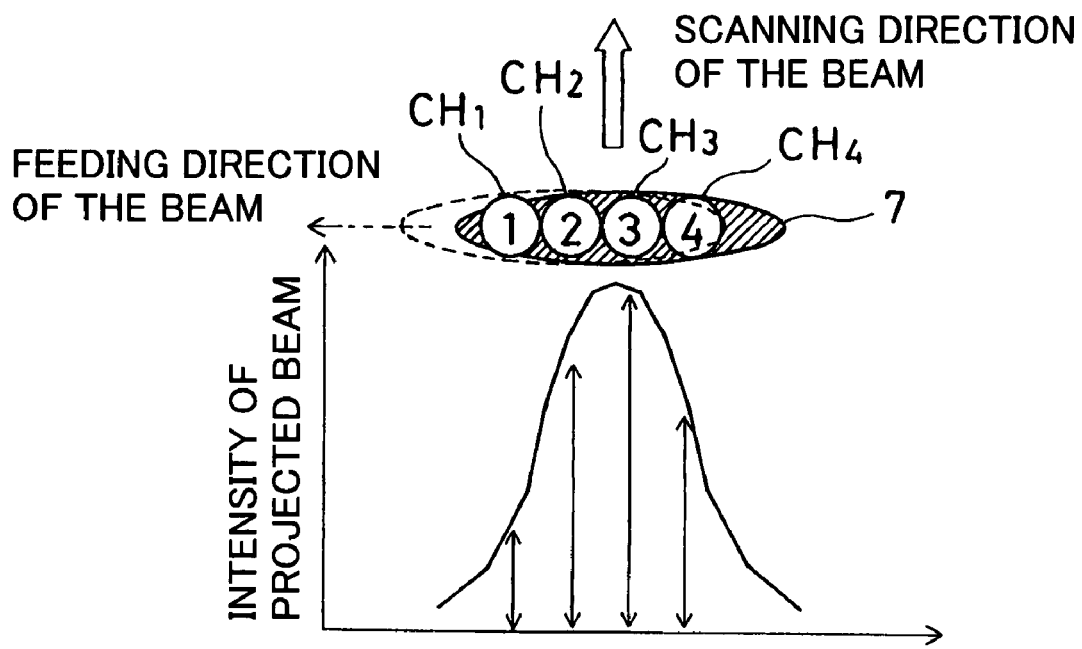
FIG. 4 is a diagram to show a relation between projection range of a laser beam and detecting regions and a relation between projection light intensity distribution and the detecting regions in a different projection light intensity distribution.

Next, FIG. 4 shows a variation of the projecting light intensity distribution of the laser beam 7.

The projection light intensity distribution is shown in a case of Gaussian distribution, which has a peak value approximately at the center. In this case, detecting regions CH1, CH2, CH3 and CH4 are set up in the projection range of the laser beam 7, and the ratio of the detection light intensities is obtained in advance on the detection light intensity when the laser beam 7 is received at each of the detecting regions. If the inspection is performed in the same manner as in the above embodiments, 4 inspection signals are obtained at the same site. As the selected signal, an output signal of all is selected, which does not exceed the proportional limit (the measurement limit) L and shows the highest value.

Figure 5:
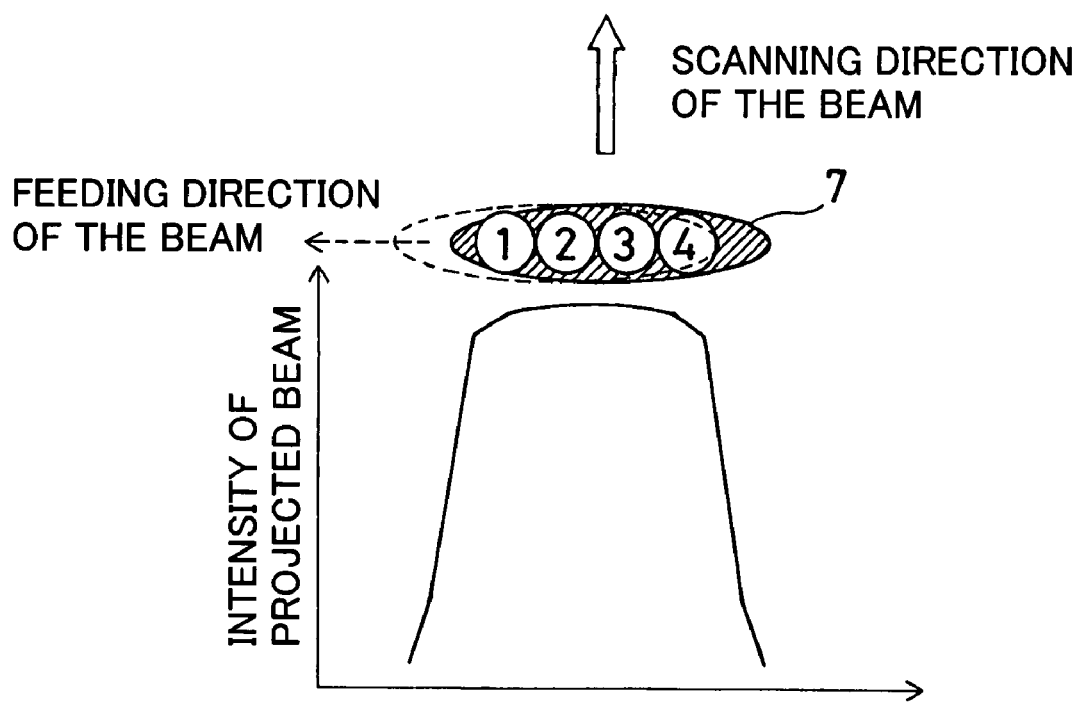
FIG. 5 is a diagram to show a relation between projection range of a laser beam and the detecting regions and a relation between projection light intensity distribution and the detecting regions in a still other different projection light intensity distribution.

FIG. 5 shows the laser beam 7, which has an other different projection light intensity distribution.

In the projection light intensity distribution shown in FIG. 5, there is no peak value, and the projection light intensity distribution is a distribution in trapezoidal shape. In this case, even if the detecting regions CH1, CH2, CH3 and CH4 are set up, no difference occurs in the receiving light intensity between the detecting regions. Accordingly, an optical filter is provided in optical path to match each of the detecting regions CH1, CH2, CH3 and CH4 so that the difference in light receiving intensity as required occurs. Or, ratio of amplification of the signals from the detecting regions CH1, CH2, CH3 and CH4 is varied, or the like so that a difference electrically develops in the output.

In case that output difference is provided at a ratio as required in the output signal from the detecting regions CH1, CH2, CH3 and CH4, the inspection can be carried out in the same manner as described above.

Figure 6:
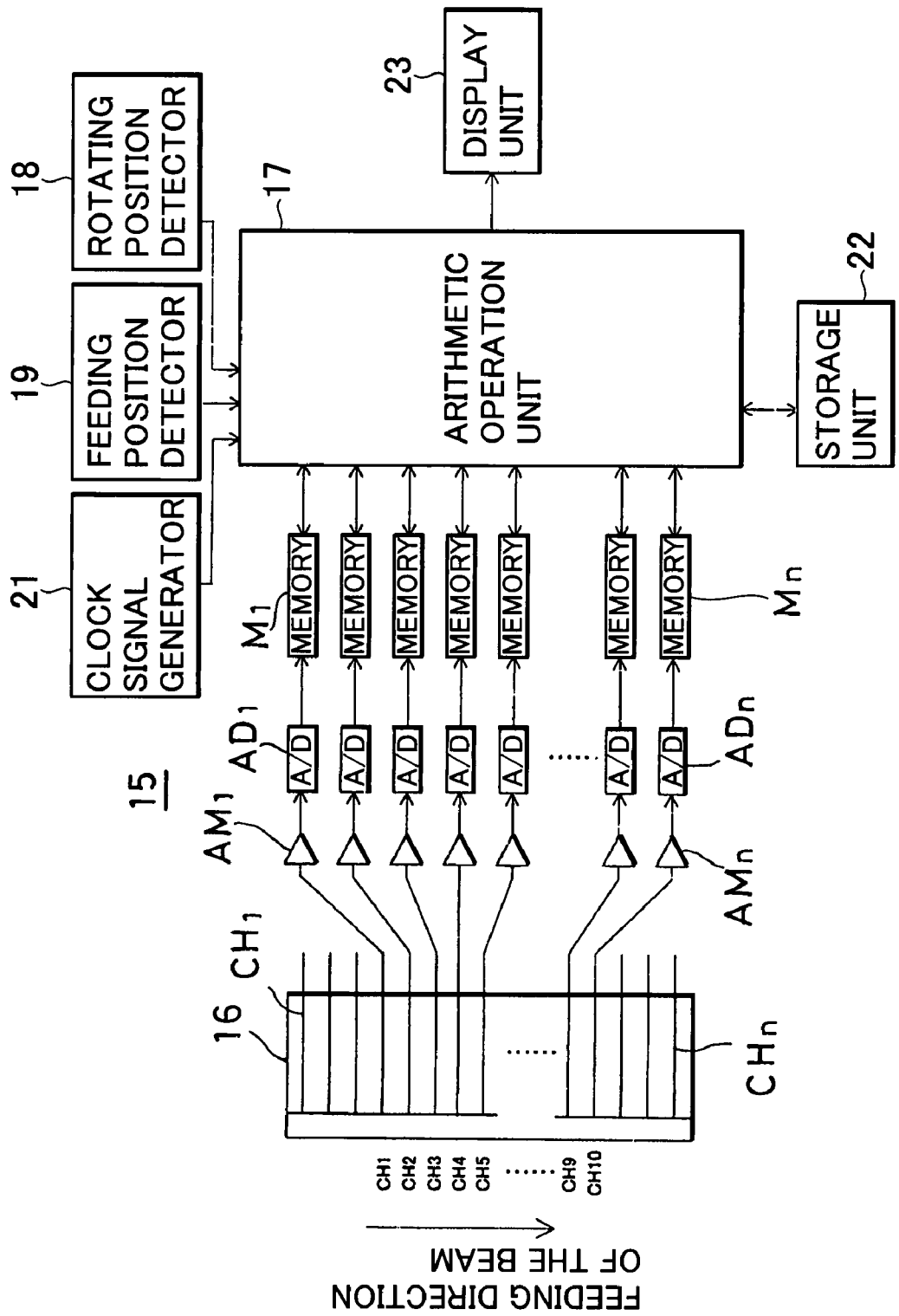
FIG. 6 is a schematical block diagram of a signal processing unit in a surface inspection device according to an embodiment of the present invention.
Figure 7:
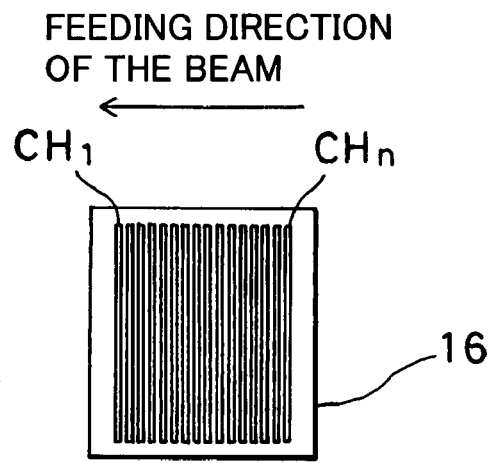
FIG. 7 is a drawing to show an example of a photodetector to be used in the present invention.

FIG. 6 is a diagram to represent approximate arrangement of a signal processing unit 15 of a surface inspection device according to the present invention. The arrangement and the structure of the surface inspection device are mainly the same as the arrangement and the structure of the device shown in FIG. 8.

In FIG. 6, reference numeral 16 denotes a photodetector 16 used in a lateral scattering light detector 9.

The photodetector 16 is an assembly of photodetection elements such as an area CCD, and each of the photodetection elements emits a photodetection signal independently.

A photodetection surface of the photodetector 16 is equally divided as required along the feeding direction of the light beam. Each of the divided portions forms detecting regions CH1-CHn respectively. Each of the detecting regions CH1-CHn independently issues output signals S1-Sn (not shown) respectively to match the detection light intensity.

Each of the output signals S1-Sn is inputted to an arithmetic operation unit 17 via amplifiers AM1-AMn, A/D converters AD1-ADn, and memory units M1-Mn. Various types of signals are inputted to the arithmetic operation unit 17. These signals include: a signal from a rotating position detector 18 for detecting a rotating position of the silicon wafer 1 (rotating position of a substrate chuck 2), a signal from a feeding position detector 19 to detect a position in radial direction of the silicon wafer (position in the feeding direction of the substrate chuck 2), and a clock signal from a clock signal generator 21.

A storage unit 22 such as a semiconductor storage unit, HDD, etc., and a display unit 23 are connected to the arithmetic operation unit 17. In the storage unit 22, various types of programs are stored such as a program to execute surface inspection based on the output signals S1-Sn, a program to turn the inspection results to images and to display the images on the display unit 23, etc. Also, the data to compare and judge flaws and foreign objects with the output signals, or the data such as the inspection results are stored. A part of the storage unit 22 may be assigned to the memory units M1-Mn.

The laser beam 7 is projected, and the silicon wafer 1 is fed at a constant speed while being rotated, and the entire surface of the inspection surface 4 is scanned by the laser beam 7.

The photodetector 16 receives a scattering light from the site where the laser beam 7 is projected. Photodetection is carried out in each of the detecting regions CH1-CHn, and output signals S1-Sn to match the detection light intensity are outputted. The detection light intensity is set so that the detection light intensity differs according to each of the detecting regions CH1-CHn. As the means to make a difference of the detection light intensity, the projection light intensity distribution is varied as described above. Or, the light is reduced optically by using filter or the like. Or, the projection light intensity distribution is varied, and further, a filter or the like is used optically and output signal of each of the detecting regions CH1-CHn is set to a ratio as required.

Each of the detecting regions CH1-CHn respectively scans the entire surface of the inspection surface 4. Output signals S1-Sn from the detecting regions CH1-CHn are stored respectively in the memory units M1-Mn by associating with rotation angle from the rotating position detector 18 and feeding position of the feeding position detector 19. Therefore, for all signals of the detecting region CH1, for instance, a position on the inspection surface 4 can be specified.

On an arbitrary position p of the inspection surface 4, the arithmetic operation unit 17 extracts an output signal Sp to match the position p from the output signals S1-Sn, and a group of "n" number of signals is obtained. From the group of "n" signals, one of the signals is selected as an inspection signal. As the signal to be selected, an output signal with the highest value not exceeding the proportional limit L is selected. The selected output signal is specified depending upon at which place in the memory units M1-Mn the output signal has been stored. Therefore, the selected signal is judged as a point represented by $S2=\beta I$ in FIG. 2, for instance. From the data of the relation between $S2=\beta I$ acquired in advance and the size of the flaw or the size of the foreign object, the flaw or the foreign object is judged based on the detected output signal, and the result is stored in the storage unit 22 as inspection data.

Extraction and selection of the above data are carried out about all points of the inspection surface 4, and inspection data on the entire surface of the inspection surface 4 can be acquired. All of the inspection data are stored in the storage unit 22. The results of inspection are turned to images by a display program and are displayed on the display unit 23.

The inspection data are acquired on the detection light intensity in the range of 0-In, referring to FIG. 2. As a result, the surface inspection is performed in the dynamic range extensively extended at least in appearance.

In case that the output signals S1-Sn are associated, the feeding speed is $\Delta t$ in the detecting regions of CHm and CHm+1. If the output signals recorded in the memory units M1-Mn are associated with the time, and the data of time delay by $\Delta t$ each time is extracted between the detecting regions CHm and CHm+1. Thus, a group Sp of "n" number of output signals to match the position p can be obtained for arbitrary point p on the inspection surface.

The selection of one signal from the output signal group Sp is the same as described above, and description is not given here.

In the above embodiment, the detecting regions are arranged in a direction to perpendicularly cross the scanning direction, while the detecting regions may be arranged in the same direction as the scanning direction. Also, it may be designed in such manner that the laser beams with different light amounts are separately projected to a plurality of sites and that the scattering light at each site is individually detected. In this case, also, output signals obtained by detecting each site is associated between the sites, and a plurality of output signals with different light intensities at the same site may be acquired.

What is claimed is:

1. A surface inspection method for projecting a laser beam to an inspection surface and for scanning and detecting foreign objects on the inspection surface, comprising the following steps:

dividing a projection range of the laser beam into two or more detection regions and performing detection with a photodetector, varying detection light intensities depending on said detecting regions, performing sequential scanning by each detection region, acquiring two or more output signals with different detection light intensities from the same inspection site through scanning of the same inspection site by each detection region, and selecting as a surface detection signal the output signal which is an unsaturated output signal and has the highest value among the two or more output signals.

2. A surface inspection method according to claim 1, wherein said laser beam is projected to have such light intensity distribution that the light intensity varies at said projected site, and two or more detecting regions are set so that detection light intensities are varied.

3. A surface inspection method according to claim 1, wherein the light amount is adjusted by an optical filter so that the detection light intensities are varied depending on said detecting regions.

4. A surface inspection method according to claim 1, wherein said detecting regions are divided with a predetermined pitch in a direction crossing to the scanning direction, and a feeding pitch of the scanning crosses perpendicularly to the scanning direction and is equal to the dividing pitch of the detection regions.

5. A surface inspection device, comprising an inspection light projecting system for projecting for scanning a laser beam to an inspection surface, a scattering light receiving system for detecting scattering lights, and an arithmetic operation unit for performing calculation to detect foreign objects based on scattering light detection output of said scattering light receiving system, wherein said scattering light receiving system performs detection of a projection range of the laser beam by dividing the projection range into two or more detection regions in such a manner that the light intensities of the scattering detection lights are varied depending on the respective detection regions, and said arithmetic operation unit selects as a surface inspection signal an unsaturated scattering light detecting output with the highest value among a plurality of scattering light detecting outputs obtained through scanning of the same site by each of two or more detection regions, wherein foreign objects are inspected based on the surface inspection signal.

6. A surface inspection device according to claim 5, wherein said inspection light projecting system projects said laser beam to have such light intensity distribution that the light intensities vary at the projected site, and said detecting regions are set so that the detection light intensities are varied.

7. A surface inspection device according to claim 5, wherein an optical filter is provided in said scattering light receiving system so that detection light intensities are varied depending on said detecting regions.

8. A surface inspection device according to claim 5, further comprising a rotating position detector, a feeding position detector, a photodetector for issuing photodetection signals individually for each region, and a memory unit arranged to match each region, wherein the photodetection signals are stored in each memory unit by associating with the rotating position and the feeding position, said arithmetic operation unit extracts a photodetection signal with the same rotating position and the same feeding position in the each memory unit and selects an unsaturated photodetection signal with said highest value as a surface inspection signal.

* * * * *